United States Patent
Ozcan et al.

(10) Patent No.: US 9,767,341 B2
(45) Date of Patent: Sep. 19, 2017

(54) METHOD AND DEVICE FOR HOLOGRAPHIC OPTO-FLUIDIC MICROSCOPY

(75) Inventors: Aydogan Ozcan, Los Angeles, CA (US); Waheb Bishara, Menlo Park, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 333 days.

(21) Appl. No.: 13/994,052

(22) PCT Filed: Dec. 13, 2011

(86) PCT No.: PCT/US2011/064701
§ 371 (c)(1),
(2), (4) Date: Jun. 13, 2013

(87) PCT Pub. No.: WO2012/082776
PCT Pub. Date: Jun. 21, 2012

(65) Prior Publication Data
US 2013/0258091 A1 Oct. 3, 2013

Related U.S. Application Data

(60) Provisional application No. 61/423,049, filed on Dec. 14, 2010.

(51) Int. Cl.
*G06K 9/00* (2006.01)
*G06T 7/00* (2017.01)
(Continued)

(52) U.S. Cl.
CPC ..... *G06K 9/00127* (2013.01); *G01N 15/1429* (2013.01); *G01N 15/1434* (2013.01);
(Continued)

(58) Field of Classification Search
CPC .. G06K 9/00127; G06K 9/00; G06K 9/00134; F03B 11/00; F03B 11/008
See application file for complete search history.

(56) References Cited

U.S. PATENT DOCUMENTS

2004/0076319 A1* 4/2004 Fauver ............... G01N 15/1468
382/133
2005/0024623 A1* 2/2005 Xie ....................... G06F 3/0317
356/3.01
(Continued)

OTHER PUBLICATIONS

Ozcan et al., Ultra wide-filed lens-free monitoring of cells on-chip, Lab on Chip 8, 89-106, Nov. 1, 2007.
(Continued)

*Primary Examiner* — Mohammed Rahaman
*Assistant Examiner* — Jimmy S Lee
(74) *Attorney, Agent, or Firm* — Vista IP Law Group LLP

(57) ABSTRACT

A method and system of imaging a moving object within a microfluidic environment includes illuminating a first side of a flow cell configured to carry the moving object within a flow of carrier fluid with an illumination source emitting at least partially coherent light, the at least partially coherent light passing through an aperture prior to illuminating the flow cell. A plurality of lower resolution frame images of the moving object are acquired with an image sensor disposed on an opposing side of the flow cell, wherein the image sensor is angled relative to a direction of flow of the moving object within the carrier fluid. A higher resolution image is reconstructed of the moving object based at least in part on the plurality of lower resolution frame images.

19 Claims, 10 Drawing Sheets

(51) Int. Cl.
*G01N 15/14* (2006.01)
*G03H 1/04* (2006.01)
*G03H 1/08* (2006.01)
*G01N 15/10* (2006.01)
*G03H 1/26* (2006.01)

(52) U.S. Cl.
CPC ....... *G01N 15/1463* (2013.01); *G03H 1/0443* (2013.01); *G06K 9/0014* (2013.01); *G06T 7/0012* (2013.01); *G01N 2015/1006* (2013.01); *G01N 2015/1075* (2013.01); *G01N 2015/1454* (2013.01); *G03H 2001/0447* (2013.01); *G03H 2001/0816* (2013.01); *G03H 2001/0825* (2013.01); *G03H 2001/2655* (2013.01); *G06T 2207/10016* (2013.01); *G06T 2207/10056* (2013.01); *G06T 2207/30242* (2013.01)

(56) References Cited

U.S. PATENT DOCUMENTS

| | | | |
|---|---|---|---|
| 2005/0237631 A1* | 10/2005 | Shioya | G06T 3/4038 359/770 |
| 2006/0215175 A1* | 9/2006 | Yacoubian | G01N 21/1717 356/502 |
| 2007/0153266 A1 | 7/2007 | Koo et al. | |
| 2007/0252986 A1* | 11/2007 | Sandstrom | G01J 4/04 356/319 |
| 2009/0117555 A1 | 5/2009 | Kuypers et al. | |
| 2009/0213238 A1* | 8/2009 | Hara | H04N 5/262 348/222.1 |
| 2010/0021042 A1* | 1/2010 | Preil et al. | 382/144 |
| 2010/0068740 A1* | 3/2010 | Kaplan | B01L 3/502707 435/14 |
| 2010/0073745 A1* | 3/2010 | Kumasawa | G03H 1/202 359/9 |
| 2010/0157422 A1* | 6/2010 | Ouchi | G02B 21/14 359/385 |
| 2010/0296094 A1 | 11/2010 | Yang et al. | |
| 2011/0033098 A1* | 2/2011 | Richter et al. | 382/131 |
| 2012/0098950 A1* | 4/2012 | Zheng | G02B 21/06 348/79 |

OTHER PUBLICATIONS

Ozcan et al., Lens-free On-Chip Cytometry for wireless Health Diagnosis, IEEE LEOS Newsletter, Oct. 2008.
Seo et al., Lensfree On-chip Cytometry Using Tunable Monochromatic Illumination and Digital Noise Reduction, Multi-color LUCAS, Sep. 2008.
Seo et al., Lensfree holographic imaging for on-chip cytometry and diagnostics, Lab on a Chip, 9, 777-787, Dec. 5, 2008.
Su et al., Towards Wireless Health: Lensless On-Chip Cytometry, Biophotonics, Dec. 2008.
Su et al., High-Throughput Lensfree Imaging and Characterization of Heterogeneous Cell Solution on a Chip, Biotechnology and Bioengineering, Sep. 8, 2008.
Isikman et al., Lensfree Cell Holography On a Chip: From Holographic Cell Signatures to Microscopic Reconstruction, LEOS Annual Meeting Conf. Proceedings, Oct. 2009.
Mudanyali et al., Lensless On-chip Imaging of Cells Provides a New Tool for High-throughput Cell-Biology and Medical Diagostics, Journal of Visualized Experiments, Dec. 14, 2009.
Coskun et al., Wide field-of-view lens-free fluorescent imaging on a chip, Lab Chip, 10(7), 824-827, Apr. 7, 2010.
Coskun et al., Lensless wide-field fluorescent imaging on a chip using compressive decoding of sparse objects, Optics Express, vol. 18 No. 10, May 5, 2010.
Khademhosseinieh et al., Lensfree color imaging on a nanostructured chip using compressive decoding, Applied Physics Letters, 97, 211112-1, Nov. 24, 2010.
Khademhosseinieh et al., Lensfree on-chip imaging using nanostructured surfaces, Applied Physics Letters, 96, 171106, Apr. 30, 2010.
Ozcan, Smart technology for global access to healthcare, SPIE, Mar. 16, 2010.
Ozcan et al., Lensfree on-chip holography facilitates novel microscopy applications, SPIE, May 19, 2010.
Bishara, W., Su, T., Coskun, A.F. & Ozcan, A. Lensfree on-chip microscopy over a wide field-of-view using pixel super-resolution. Opt. Express 18, 11181 (2010).
Chin, C.D., Linder, V. & Sia, S.K. Lab-on-a-chip devices for global health: Past studies and future opportunities. Lab Chip 7, 41 (2007).
Craighead, H. Future lab-on-a-chip technologies for interrogating individual molecules. Nature 442, 387-393 (2006).
Cui, X. et al. Lensless high-resolution on-chip opto-fluidic microscopes for Caenorhabditis elegans and cell imaging. Proc. Natl. Acad. Sci. 105, 10670-10675 (2008).
Dittrich, P.S. & Manz, A. Lab-on-a-chip: microfluidics in drug discovery. Nat Rev Drug Discov 5, 210-218 (2006).
Dong, L., Agarwal, A.K., Beebe, D.J. & Jiang, H. Adaptive liquid microlenses activated by stimuli-responsive hydrogels. Nature 442, 551-554 (2006).
El-Ali, J., Sorger, P.K. & Jensen, K.F. Cells on chips. Nature 442, 403-411 (2006).
Garcia-Sucerquia, J., Xu, W., Jericho, M.H. & Kreuzer, H.J. Immersion digital in-line holographic microscopy. Opt. Lett. 31, 1211 (2006).
Haddad, W.S. et al. Fourier-transform holographic microscope. Appl. Opt. 31, 4973 (1992).
Haeberle, S. & Zengerle, R. Microfluidic platforms for lab-on-a-chip applications. Lab Chip 7, 1094 (2007).
Hardie, R.C. et al. High-resolution image reconstruction from a sequence of rotated and translated frames and its application to an infrared imaging system. Opt. Eng. 37, 247 (1998).
Hardie, R., Barnard, K. & Armstrong, E. Joint MAP registration and high-resolution image estimation using a sequence of undersampled images. IEEE Trans. on Image Process. 6, 1621-1633 (1997).
Heng, X. et al. Opto-fluidic microscopy—a method for implementing a high resolution optical microscope on a chip. Lab Chip 6, 1274-1276 (2006).
Lee, L.M., Cui, X. & Yang, C. The application of on-chip opto-fluidic microscopy for imaging Giardia lamblia trophozoites and cysts. Biomed Microdevices (2009).doi:10.1007/s10544-009-9312-x.
Lew, M., Cui, X., Heng, X. & Yang, C. Interference of a four-hole aperture for on-chip quantitative two-dimensional differential phase imaging. Opt. Lett. 32, 2963 (2007).
Li, Z., Zhang, Z., Emery, T., Scherer, A. & Psaltis, D. Single mode opto-fluidic distributed feedback dye laser. Opt. Express 14, 696 (2006).
Monat, C., Domachuk, P. & Eggleton, B.J. Integrated opto-fluidics: A new river of light. Nature Photon 1, 106-114 (2007).
Mudanyali, O. et al. Compact, light-weight and cost-effective microscope based on lensless incoherent holography for telemedicine applications. Lab Chip 10, 1417 (2010).
Oh, C., Isikman, S.O., Khademhosseinieh, B. & Ozcan, A. On-chip differential interference contrast microscopy using lensless digital holography. Opt. Express 18, 4717 (2010).
Sung Cheol Park, Min Kyu Park & Moon Gi Kang Super-resolution image reconstruction: a technical overview. IEEE Signal Process. Mag. 20, 21-36 (2003).
Psaltis, D., Quake, S.R. & Yang, C. Developing opto-fluidic technology through the fusion of microfluidics and optics. Nature 442, 381-386 (2006).
Su, T. et al. Multi-angle lensless digital holography for depth resolved imaging on a chip. Opt. Express 18, 9690 (2010).
Squires, T. & Quake, S. Microfluidics: Fluid physics at the nanoliter scale. Rev. Mod. Phys. 77, 977-1026 (2005).
Weigl, B. Lab-on-a-chip for drug development. Advanced Drug Delivery Reviews 55, 349-377 (2003).
Whitesides, G.M. The origins and the future of microfluidics. Nature 442, 368-373 (2006).

(56) References Cited

OTHER PUBLICATIONS

Woods, N., Galatsanos, N. & Katsaggelos, A. Stochastic methods for joint registration, restoration, and interpolation of multiple undersampled images. IEEE Trans. on Image Process. 15, 201-213 (2006).

Xu, W. Digital in-line holography for biological applications. Proc. Natl. Acad. Sci. 98, 11301-11305 (2001).

Zheng, G., Cui, X. & Yang, C. Surface-wave-enabled darkfield aperture for background suppression during weak signal detection Proc. Natl. Acad. Sci. 107, 9043-9048 (2010).

PCT International Search Report for PCT/US2011/064701, Applicant: The Regents of the University of California, Form PCT/ISA/210 and 220, dated Jul. 18, 2012 (5pages).

PCT Written Opinion of the International Search Authority for PCT/US2011/064701, Applicant: The Regents of the University of California, Form PCT/ISA/237, dated Jul. 18, 2012 (6pages).

Yang, C. and Psaltis, D., Optofluidic can create small, cheap biopthotonic devices, Laser Focus World, Jul. 2006, pp. 85-87.

Luenberger, D.G., Linear and Nonlinear Programming. Addison-Wesley: Reading Mass., 1984 (10pages).

PCT International Preliminary Report on Patentability (Chapter I of the Patent Cooperation Treaty) for PCT/US2011/064701, Applicant: The Regents of the University of California, Form PCT/IB/326 and 373, dated Jun. 18, 2013 (7pages).

\* cited by examiner

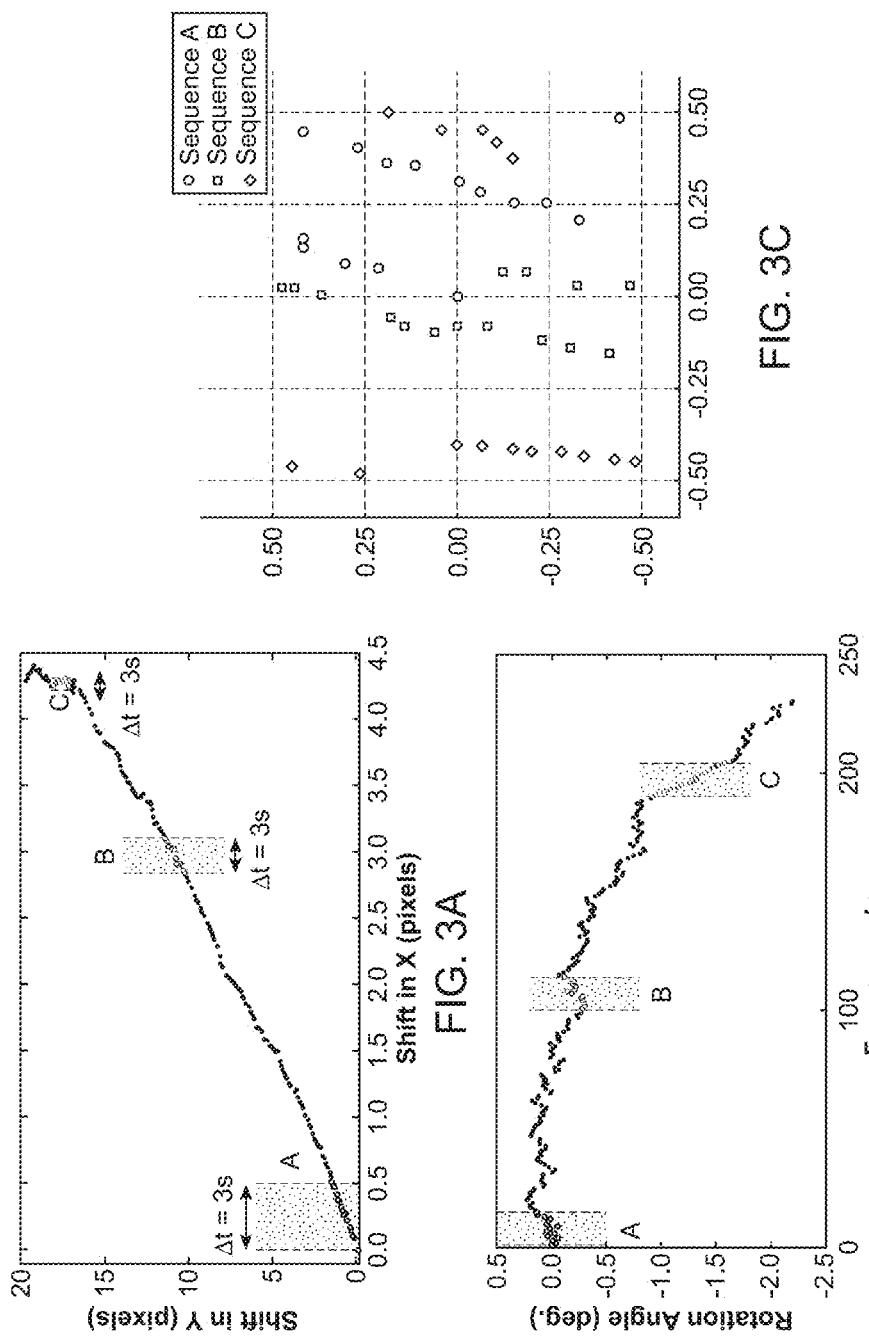

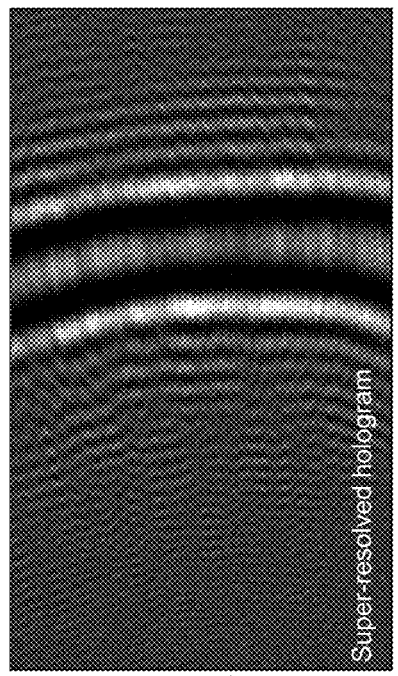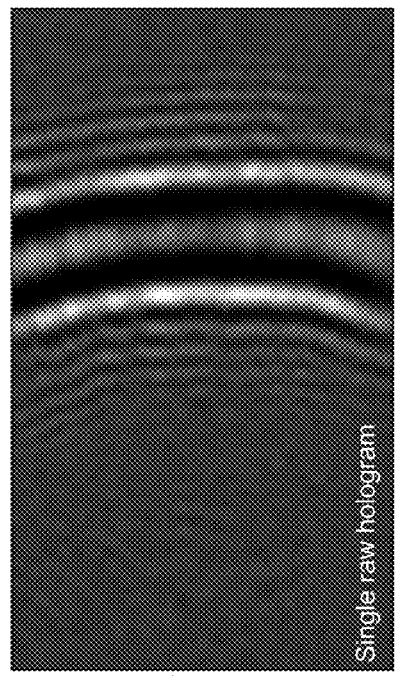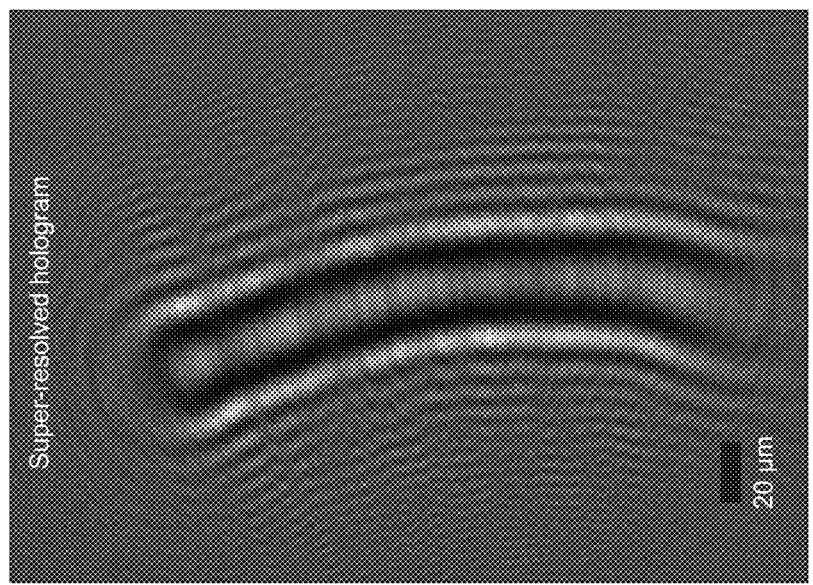

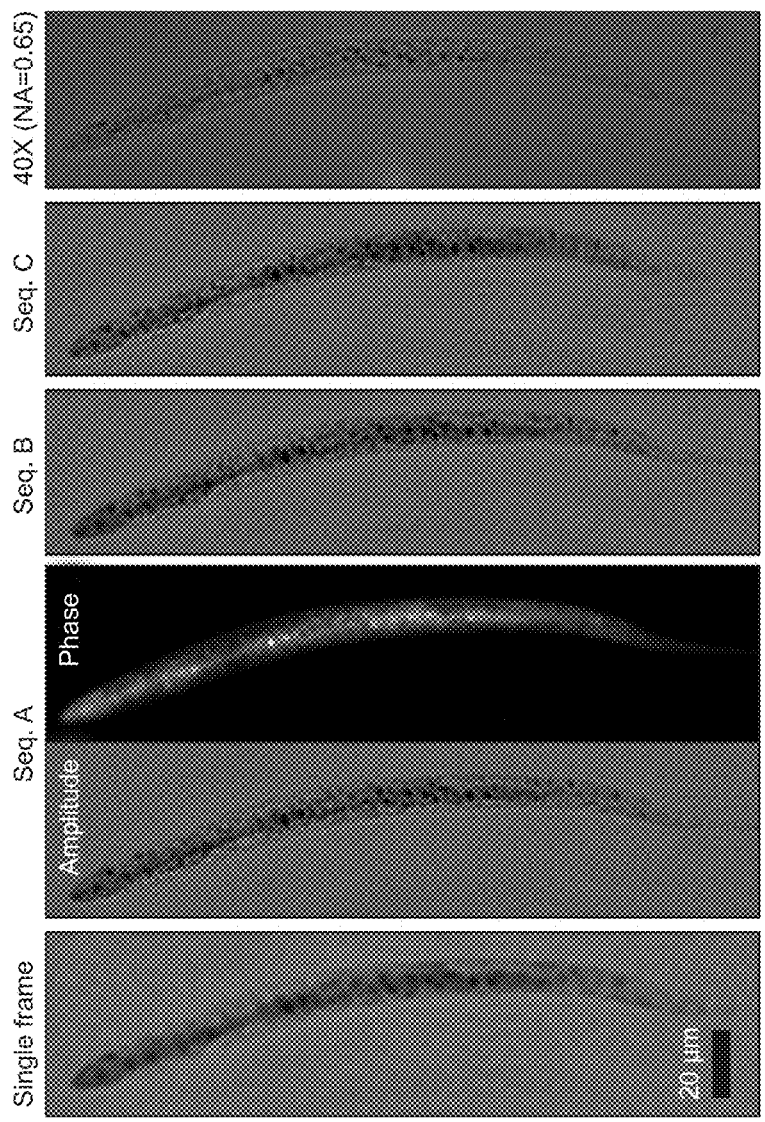

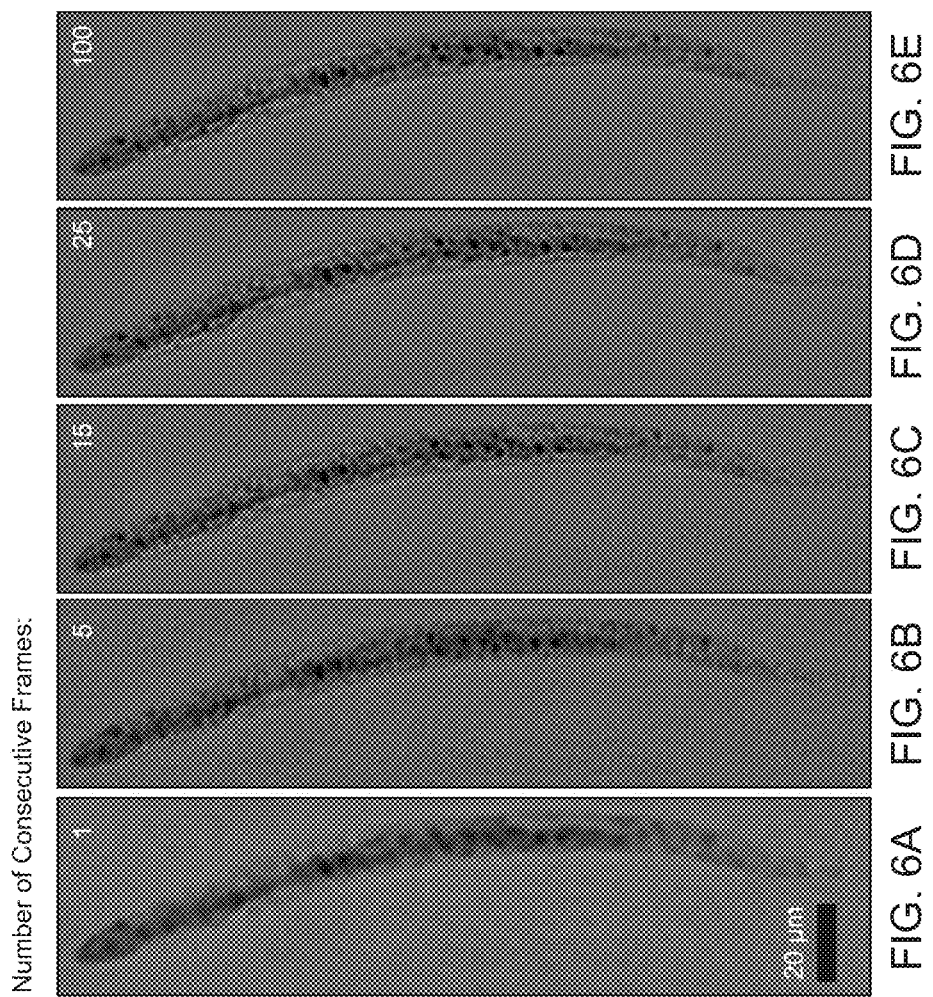

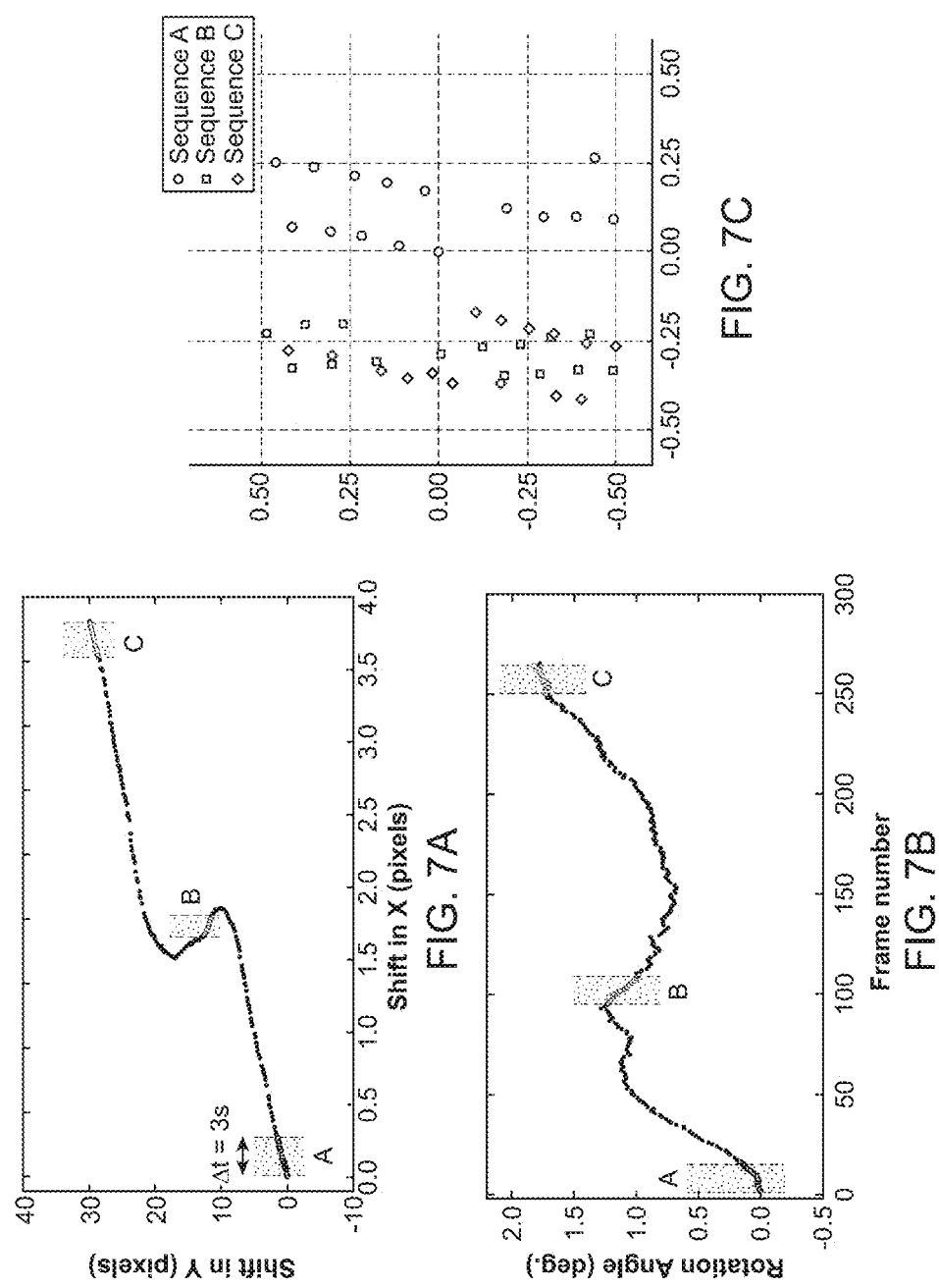

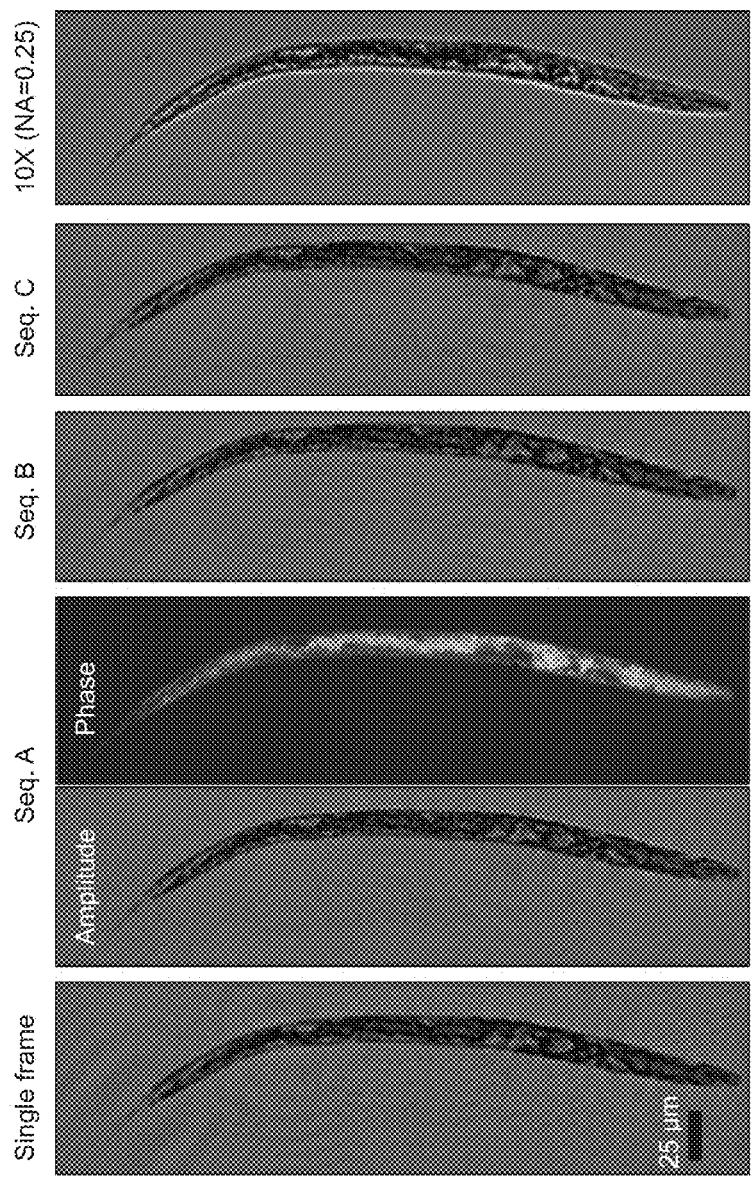

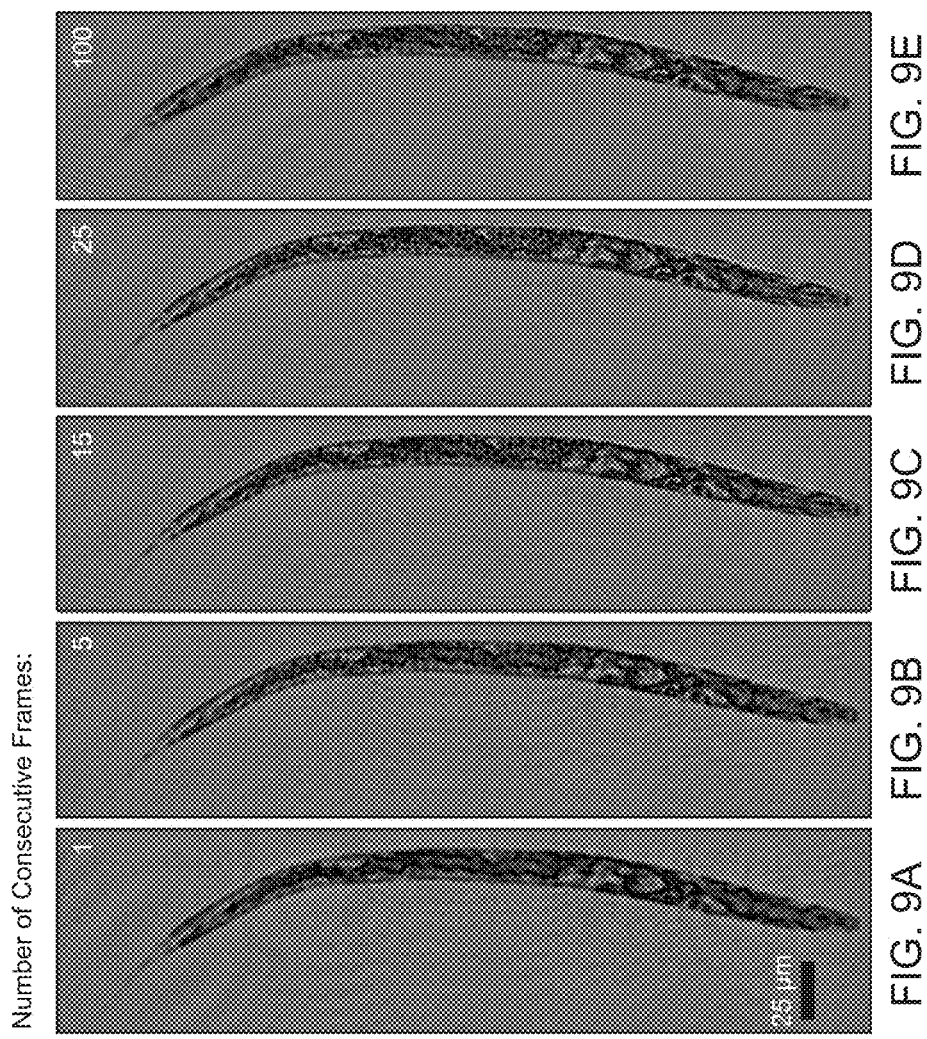

METHOD AND DEVICE FOR HOLOGRAPHIC OPTO-FLUIDIC MICROSCOPY

RELATED APPLICATION

This Application is a U.S. National Stage filing under 35 U.S.C. §371 of International Application No. PCT/US2011/064701, filed Dec. 13, 2011, which claims priority to U.S. Provisional Patent Application No. 61/423,049 filed on Dec. 14, 2010. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

FIELD OF THE INVENTION

The field of the invention generally relates to methods and devices for imaging of microscopic structures such as cells and particles. More particularly, the field of the invention pertains to systems and methods for the imaging of cells or particles flowing within a microfluidic environment.

BACKGROUND

Opto-fluidics is a recently emerging field that aims to merge the available toolset of optics and microfluidics to create more flexible and reconfigurable optical devices with novel functionalities that can provide a better fit to especially lab-on-a-chip platforms. The cost-effectiveness and compactness of lab-on-a-chip devices when combined with throughput and sensitivity have already enabled powerful solutions to a wide range of biomedical problems. Creation of new opto-fluidic technologies would further enhance the performance and functionality of existing lab-on-a-chip platforms, and toward this end various opto-fluidic devices have been demonstrated including tunable lasers, lenses, waveguides and sensors. Microfluidics enabled on-chip digital microscopy could especially be important for global health problems to assist diagnosis of disease (e.g., malaria, tuberculosis) in remote locations, and holds significant promise not only for point-of-care operation but also for telemedicine applications.

Opto-Fluidic Microscopy (OFM) is a microfluidic imaging concept that came out of this emerging field, which aims to image objects flowing within a micro-fluidic channel without the use of any lenses. These OFM systems abandon conventional microscope design, which requires expensive lenses and large space to magnify the images, and instead uses microfluidic flow to deliver specimens across array(s) of micrometer-sized apertures defined on a metal-coated CMOS sensor to generate direct projection images. For example, such as system is disclosed in Cui et al., Lensless high-resolution on-chip opto-fluidic microscopes for *Caenorhabditis elegans* and cell imaging. Proc. Natl. Acad. Sci. 105, 10670-10675 (2008). Thus, conventional OFM designs rely on a digital sensor-array, such as a complementary metal-oxide semiconductor (CMOS) or a charge-coupled device (CCD) chip, which is placed directly underneath the micro-fluidic channel to sample the transmitted light that passes through the flowing object. To overcome the limited spatial resolution dictated by relatively large pixel size at the sensor-chip, OFM utilizes a slanted micro or nano-sized aperture array fabricated on the active area of the sensor, such that under controlled flow conditions, the spatial resolution becomes independent of the pixel size yielding high-resolution reconstructed digital images. OFM thus has additional manufacturing complexity given the need for the aperture array atop of the imaging sensor.

OFM images the transmission intensity of the objects specifically at the aperture plane (within 1-2 µm depth) and cannot yet achieve depth focusing or backward wave propagation as it lacks complex wave information. Because of this, the microfluidic channel of OFM-based devices needs to be fabricated very close to the active region of the CMOS or CCD sensor which necessitates the mechanical removal of the protective cover glass of the sensor. Another limitation of OFM is that it demands that the position of the object be constant with respect to the microchannel cross-section. Often, however, cells or particles within a microfluidic flowing environment experience lateral shifting during flow.

An on-chip imaging system and method that does not require fabrication of complicated apertures on a chip, nor demands distortion-free motion of the objects within the microchannel would be particularly useful. This would significantly improve the practical implementations of lens-free opto-fluidic on-chip imaging, while also significantly increasing the light collection efficiency.

SUMMARY

In one embodiment, an imaging platform is described that conducts lens-free opto-fluidic microscopy. The imaging platform relies on partially coherent digital in-line holography and pixel super-resolution to create high-resolution on-chip images of objects such as cells or particles that are flowing within a microfluidic channel. In this approach, a spatially coherent or partially coherent visible light source (quasi-monochromatic with a spectral bandwidth of e.g., ~5 nm) illuminates the objects within a microfluidic channel or flow cell. Within a few centimeters of free-space propagation, the illumination light picks up partial spatial coherence, the extent of which is sufficient to record lens-free in-line holograms of the objects flowing within the microfluidic channel. Each lens-free hologram is created by the interference of the scattered waves from the moving object with the background light, which acts a reference wave. When compared to standard lens-free in-line holograph approaches, the imaging platform described herein has several unique advantages such as simplicity to align and operate, significantly larger field of view, as well as reduced speckle and multiple-interference noise terms.

The lens-free holograms of the objects are then digitally sampled by the sensor-array (e.g., a CMOS chip) which is placed at a slight angle with respect to the flow direction. Because of the unit fringe magnification of the imaging geometry, depending on the pixel size at the sensor, the acquired holograms may be under-sampled. On the other hand, since during the flow each lens-free object hologram is sampled with different sub-pixel shifts as a function of time, one can use a pixel super-resolution algorithm to digitally synthesize a high-resolution hologram that has an effective pixel size of which is significantly smaller than the physical pixel size of the sensor (e.g. >2 µm). For example, an effective pixel size of e.g., ≤0.5 µm can be achieved.

The flow of the object within the microchannel is used to digitally create smaller pixels for hologram sampling. Such a super-resolved digital in-line hologram, after elimination of the twin-image artifact, enables high-resolution lens-free imaging of the objects within the microfluidic flow. Unlike existing opto-fluidic microscope designs such as OFM, this platform neither requires fabrication of on-chip apertures, nor demands distortion-free flow of the objects, both of which are rather important to simplify practical implementations of opto-fluidic on-chip microscopy, while also significantly increasing the light collection efficiency. In addition, because this platform permits digital recovery of the complex optical fields with sub-pixel resolution, it also enables backward wave-propagation and depth focusing to be performed digitally, which offers various advantages for the design, fabrication and operation of the opto-fluidic microscope.

In one embodiment, a system for imaging a moving object within a microfluidic environment includes a flow cell configured to carry the moving object within a flow of carrier fluid; an illumination source configured to illuminate a first side of the flow cell through a spatial filter interposed between the illumination source and the flow cell; and an image sensor disposed on a second, opposite side of the flow cell, wherein the image sensor is angled relative to a direction of flow of the moving object within the carrier fluid.

In another embodiment, a method of imaging a moving object within a microfluidic environment includes illuminating a first side of a flow cell configured to carry the moving object within a flow of carrier fluid with an illumination source emitting at least partially coherent light, the at least partially coherent light passing through an aperture prior to illuminating the flow cell; acquiring a plurality of lower resolution frame images of the moving object with an image sensor disposed on an opposing side of the flow cell, wherein the image sensor is angled relative to a direction of flow of the moving object within the carrier fluid; and reconstructing a higher resolution image of the moving object based at least in part on the plurality of lower resolution frame images.

BRIEF DESCRIPTION OF THE DRAWINGS

FIG. 3A illustrates the two-dimensional lateral shifts of consecutive holographic frames with respect to the first one for electro-kinetic fluid flow. Sequences A, B, and C which each include fifteen consecutive frames are also illustrated.

FIG. 3B illustrates in-plane rotation angles of consecutive holographic frames with respect to the first one for electro-kinetic fluid flow. Sequences A, B, and C which each include fifteen consecutive frames are also illustrated.

FIG. 3C illustrates the relative shifts of the holographic frames (FIGS. 3A and 3B) with respect to the first frame of each sequence (Sequence A: circle data points, Sequence B: square data points and Sequence C: diamond data points). In FIG. 3C, only the sub-pixel shifts are shown, since any integer number of pixel shifts does not contain additional information for synthesis of a super-resolved hologram. These were digitally subtracted out for the data of FIG. 3C.

FIG. 4A illustrates a super-resolved, high resolution hologram image using Sequence A.

FIG. 4B illustrates an enlarged section of FIG. 4A where sub-pixel holographic oscillation is observed.

FIG. 4C illustrates a single lens-free raw hologram (low resolution) image of the same worm to better present the increased fringe visibility of the synthesized hologram.

FIG. 5A illustrates a single raw lens-free hologram at a lower resolution image of the object after twin image elimination.

FIG. 5B illustrates the higher resolution amplitude and phase images of the worm using Sequence A.

FIG. 5C illustrates the reconstruction results (high resolution amplitude image) of Sequence B.

FIG. 5D illustrates the reconstruction results (high resolution amplitude image) of Sequence C.

FIG. 5E illustrates a conventional transmission microscope image of the same sample acquired using a 40× objective lens (NA=0.65).

FIG. 6A illustrates the super pixel resolution image of a moving object (electro-kinetically driven) using one frame as the input.

FIG. 6B illustrates the high resolution image of a moving object (electro-kinetically driven) using five consecutive frames as the input.

FIG. 6C illustrates the high resolution image of a moving object (electro-kinetically driven) using fifteen consecutive frames as the input.

FIG. 6D illustrates the high resolution image of a moving object (electro-kinetically driven) using twenty five consecutive frames as the input.

FIG. 6E illustrates the high resolution image of a moving object (electro-kinetically driven) using one hundred consecutive frames as the input.

FIG. 7A illustrates the two-dimensional lateral shifts of consecutive holographic frames with respect to the first one for pressure fluid flow. Sequences A, B, and C which each include fifteen consecutive frames are also illustrated.

FIG. 7B illustrates in-plane rotation angles of consecutive holographic frames with respect to the first one for pressure fluid flow. Sequences A, B, and C which each include fifteen consecutive frames are also illustrated.

FIG. 7C illustrates the relative shifts of the holographic frames (FIGS. 7A and 7B) with respect to the first frame of each sequence (Sequence A: circle data points, Sequence B: square data points and Sequence C: diamond data points).

FIG. 8A illustrates a single raw lens-free hologram at a lower resolution image of the object after twin image elimination (pressure driven flow used).

FIG. 8B illustrates the higher resolution amplitude and phase images of the worm using Sequence A (pressure driven flow used).

FIG. 8C illustrates the reconstruction results (high resolution amplitude image) of Sequence B (pressure driven flow used).

FIG. 8D illustrates the reconstruction results (high resolution amplitude image) of Sequence C (pressure driven flow used).

FIG. 8E illustrates a conventional transmission microscope image of the same sample acquired using a 10× objective lens (NA=0.25).

FIG. 9A illustrates the super pixel resolution image of a moving object (pressure driven) using one frame as the input.

FIG. 9B illustrates the high resolution image of a moving object (pressure driven) using five consecutive frames as the input.

FIG. 9C illustrates the high resolution image of a moving object (pressure driven) using fifteen consecutive frames as the input.

FIG. 9D illustrates the high resolution image of a moving object (pressure driven) using twenty five consecutive frames as the input.

FIG. 9E illustrates the high resolution image of a moving object (pressure driven) using one hundred consecutive frames as the input.

DETAILED DESCRIPTION OF THE ILLUSTRATED EMBODIMENTS

Figure 1:
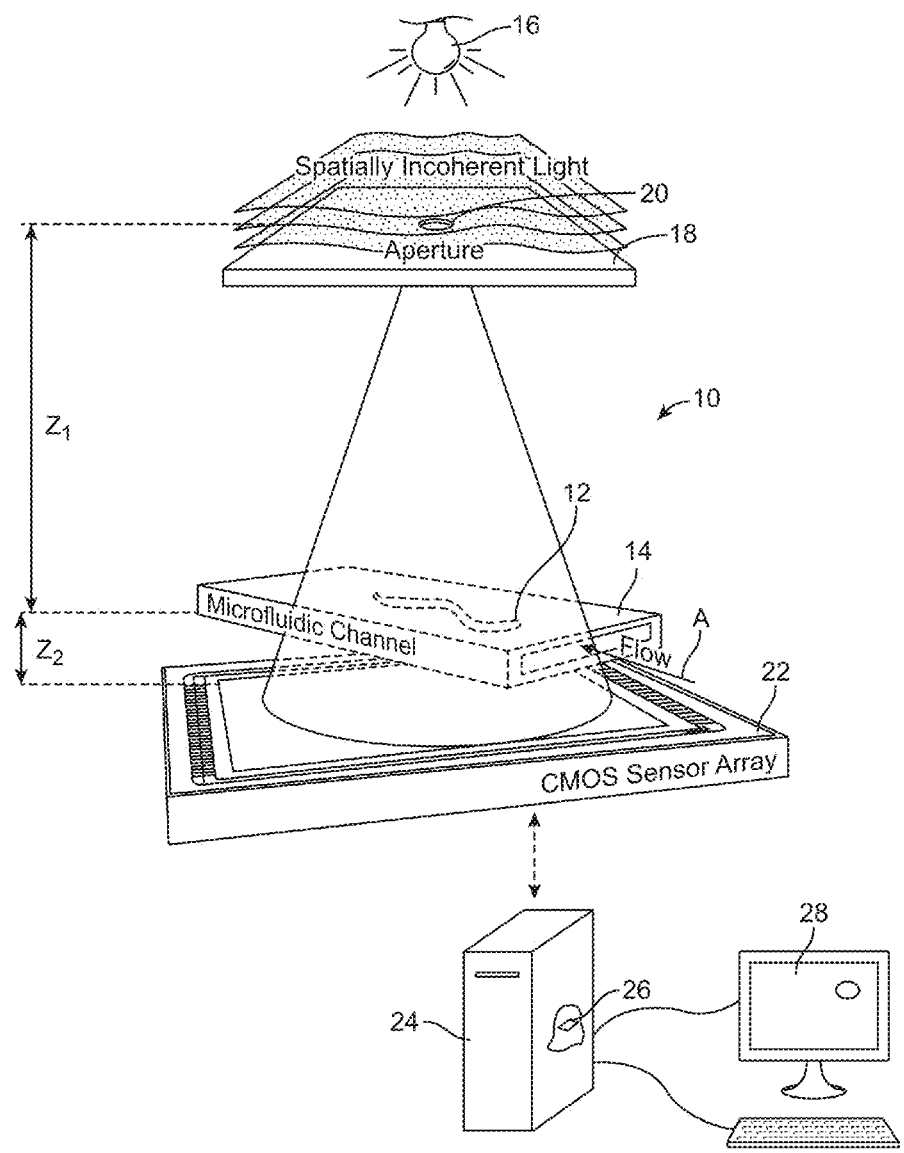
FIG. 1 illustrates a system for imaging a moving object within a microfluidic environment according to one embodiment.

FIG. 1 illustrates a system 10 for imaging a moving object 12 within a microfluidic environment according to one embodiment. The system 10 includes a flow cell 14 that is configured to carry the moving object 12 within a flow of a carrier fluid. In one aspect, the moving object 12 may include a cell or other biological component. The moving object 12 may also include a non-biological particle or the like. The carrier fluid is typically a liquid in which the moving object resides. The carrier fluid could also be a gas in some circumstances. When the moving object 12 is a cell, the carrier fluid is typically a physiological compatible buffer solution or the like (e.g., phosphate buffered saline). The flow cell 14 is a substantially straight, three-dimensional conduit that is substantially optically transparent (at least with respect to source of illumination described in more detail herein). The flow cell 14 may be made from glass, plastic, or other materials commonly used in connection with microfluidic devices. The conduit of the flow cell 14 may have a regularly-shaped cross-sectional area such as a square or rectangle. The internal dimensions of the flow cell 14 that contain the moving object 12 may vary. For example, the flow cell 14 may have heights/widths that are on the millimeter scale. Alternatively, the flow cell 14 may have heights/widths that are on the micrometer scale. In this regard, the flow cell 14 may include a microchannel or the like.

The moving objects 12 are moved or flowed through the flow cell 14 using one or more pumping techniques. For example, a pressure gradient may be established to pump fluid containing objects 12 within flow cell 14. Alternatively, the moving objects 12 may be moved through the flow cell 14 using electro-kinetic motion with electrodes at opposing ends of the flow cell 14 being used. In this regard, any particular pumping modality may be used to move the objects 12 through the flow cell 14. Examples include the use of pumps like syringe pumps, dielectrophoresis based electrodes, magnetohydrodynamic electrodes, and the like.

Still referring to FIG. 1, the system 10 includes an illumination source 16 that is configured to illuminate a first side (top side as seen in FIG. 1) of the flow cell 14. The illumination source 16 is preferably a spatially coherent or a partially coherent light source. Light emitting diodes (LEDs) are one example of an illumination source 16. LEDs are relative inexpensive, durable, and have generally low power requirements. Of course, other light sources may also be used such as a Xenon lamp with a filter. A laser or a light bulb are also options as the illumination source 16. The illumination source 16 preferably has a spectral bandwidth that is between about 0.1 and about 100 nm, although the spectral bandwidth may be even smaller or larger. Further, the illumination source 16 may include at least partially coherent light having a spatial coherence diameter between about 0.1 to 10,000 µm.

As seen in FIG. 1, a spatial filter 18 is interposed between the illumination source 16 and the flow cell 14. The spatial filter 18 has an aperture 20 contained therein that is configured to permit the passage of illumination. The aperture 20 has a diameter (D) that is typically in the range of 50 µm to about 100 µm.

As seen in FIG. 1, an image sensor 22 is disposed on a second, opposite side of the flow cell 14 such that the flow cell 14 is interposed between the illumination source 16 and the image sensor 22. The image sensor 22 is located adjacent to the back side of the flow cell 14. The surface of image sensor 22 may be in contact with or close proximity to the back side of the flow cell 14. For example, the flow cell 14 may be placed directly atop the glass or other optically transparent layer that typically covers the image sensor 22. The image sensor 22 may include, for example, a charged coupled device (CCD) or a complementary metal-oxide semiconductor (CMOS) device. The image sensor 22 may be monochromatic or color. The image sensor 22 generally has a small pixel size which is less than 9.0 µm in size and more particularly, smaller than 5.0 µm in size (e.g., 2.2 µm or smaller). Generally, image sensors 22 having smaller pixel size will produce higher resolutions. One benefit of the imaging method described herein is that a spatial resolution better than pixel size can be obtained.

Still referring to FIG. 1, the spatial filter 18 is located at a distance $z_1$ from the flow cell 14. The imaging plane of the image sensor 22 is located at a distance $z_2$ from the flow cell 14. In the system 10 described herein, $z_2 \ll z_1$. For example, the distance $z_1$ may be on the order of around 1 cm to around 10 cm. In other embodiments, the range may be smaller, for example, between around 5 cm to around 10 cm. The distance $z_2$ may be on the order of around 0.05 mm to 2 cm, however, in other embodiments this distance $z_2$ may be between around 1 mm to 2 mm. In the system 10, the propagation distance $z_1$ is such that it allows for spatial coherence to develop at the plane of the moving object 12, and light scattered by the moving object 12 interferes with background light to form a lens-free in-line hologram on the image sensor 22.

As seen in FIG. 1, the moving objects 12 flow within the flow cell 14 in the direction of arrow A. Arrow A is substantially parallel with the long axis of the flow cell 14. The direction of flow A (and thus the flow cell 14) is slightly angled relative to the image sensor 22. The exact value of this angle is not critical and need not be known a priori; it simply ensures that the flow of the moving object 12 along the flow cell 14 will generate a shift component in both axes directions, x and y of the image sensor 22. The angle should generally be between a non-zero angle and less than 45°.

Still referring to FIG. 1, the system 10 includes a computer 24 such as a laptop, desktop, or the like that is operatively connected to the system 10 such that lower resolution images (e.g., lower resolution or raw image frames) are transferred from the image sensor 22 to the computer 24 for data acquisition and image processing. The computer 24 includes one or more processors 26 that, as described herein in more detail, runs or executes software that acquires an image of the moving object(s) 12 that includes the holographic amplitude or intensity. The software on the computer 24 then recovers the lost phase of the image. Having both the holographic amplitude and recovered phase of the same image, the software then reconstructs a higher resolution image of the moving object(s) 12. This reconstructed image can be displayed to the user on, for example, a display 28 or the like. The software may also identify and display particular cells of interest based on their holographic signature.

Moving objects 12 that flow through the flow cell 14 are imaged using the image sensor 22. In particular, a plurality of low resolution holographic image frames is acquired using the angularly offset image sensor 22. Because of the unit fringe magnification of the system imaging geometry, depending on the pixel size at the image sensor 22, the acquired holograms may be under-sampled. On the other hand, since during the flow each lens-free object hologram is sampled with different sub-pixel shifts as a function of time, one can use a pixel super-resolution algorithm to digitally synthesize a high-resolution hologram that has an effective pixel size of e.g., ≤0.5 µm, which is significantly smaller than the physical pixel size of the sensor (e.g., >2 µm). Thus, the system uses the flow of the moving object 12 within the flow cell 14 to digitally create smaller pixels for hologram sampling. Such a super-resolved digital in-line hologram, after elimination of the twin-image artifact, enables high-resolution lens-free imaging of the moving objects 12.

Figure 2:
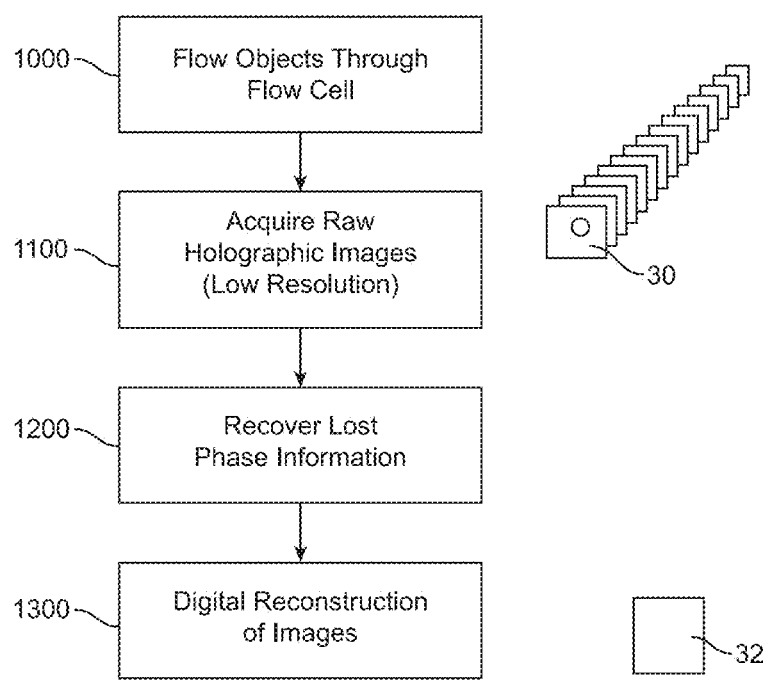
FIG. 2 illustrates a flow chart of the sequence of operations for the generation of a high resolution image of a moving object from a plurality of lower resolution image frames.

FIG. 2 illustrates a top-level flowchart of how the system 10 digitally reconstructs an image of the moving object 12. As seen in operation 1000 of FIG. 2, a moving object 12 is flowed or otherwise moved through the flow cell 14. Raw holographic images are then obtained in operation 1100 using the angled image sensor 22. FIG. 2 illustrates fifteen (15) such image frames 30 being captured, which as explained herein, is enough to produce a high resolution reconstruction of the image. It should be understood that the angling of the image sensor 22 relative to the flow direction of the moving objects 12 creates a shift component in both the sensor axes directions (x and y). The "lost" phase information is then recovered in operation 1200. Based on the recovered phase information and the raw holographic images, one or more higher resolution images of the moving objects 12 are then digitally reconstructed as outlined in operation 1300. FIG. 2 illustrates a higher resolution image frame 32.

With regard to lateral and rotational (in-plane) translation of the moving object 12, the computer 24 simultaneously computes the lateral translation and angular rotation between consecutive frames 30 using a local gradient-based iterative algorithm applied to a 50×50 pixel region located at the center of the holographic pattern of interest. Details of this local gradient-based iterative algorithm may be found in Hardie, R. C. et al., High-resolution image reconstruction from a sequence of rotated and translated frames and its application to an infrared imaging system. Opt. Eng. 37, 247 (1998), which is incorporated herein by reference.

To provide more details on this numerical step, let one consider a lateral translation of ($\Delta_x$, $\Delta_y$) and a rotation angle of $\theta$, applied to a two-dimensional image f(x, y). This operation transforms f(x, y) to g(x, y) such that:

$$f(x,y) \rightarrow g(x,y) = f(x \cos\theta - y \sin\theta + \Delta_x, x \sin\theta + y \cos\theta + \Delta_y) \quad (1)$$

For small translations and a small rotation angle (which are applicable for consecutive raw holograms), the rotated and shifted image can be approximated by using the original image and its derivatives:

$$g(x, y) \approx \tilde{g}(x, y) = f(x, y) + \left(\frac{\partial f}{\partial x}\right)(\Delta_x - y\theta) + \left(\frac{\partial f}{\partial y}\right)(\Delta_y + x\theta) \quad (2)$$

Therefore, for a given image f(x, y), its derivatives can be numerically calculated to find the best estimate of ($\Delta_x$, $\Delta_y$, $\theta$) which minimizes the square error between the measured image g(x, y) and its approximation $\tilde{g}$(x, y). Accordingly, the error (E) that is intended to be minimized can be written as:

$$E = \sum_{all\ pixels} (g(m, n) - \tilde{g}(m, n))^2 \quad (3)$$

$$= \sum_{all\ pixels} \left(g(m, n) - f(m, n) + \left(\frac{\partial f}{\partial x}\right)(\Delta_x - n\theta) + \left(\frac{\partial f}{\partial y}\right)(\Delta_y + m\theta)\right)^2$$

where m and n are integers labeling the pixels of the images. The derivatives of f(m, n) can be readily calculated by convolution with a Sobel operator for example, leaving only ($\Delta_x$, $\Delta_y$, $\theta$) as the unknowns in Eq. (3). Differentiating Eq. (3) with respect to the unknowns and equating the derivatives to zero in search of the function minimum results in an algebraic equation which can be solved to yield an estimate of the image shifts and rotation ($\hat{\Delta}_x$, $\hat{\Delta}_y$, $\hat{\theta}$).

Quite conveniently, this initial shift estimate can also be iteratively refined. For instance, once an estimate ($\hat{\Delta}_x$, $\hat{\Delta}_y$, $\hat{\theta}$) is obtained as discussed above, the image f(m, n) can be interpolated to a new shifted and rotated grid according to the estimate, leading to a new image $f_2$(m, n) which is by construction closer to the measured image, g(m, n). The same steps described above can now be performed once again to estimate the lateral shift and rotation this time between $f_2$(m, n) and g(m, n). This step enables further refinement of the shift and rotation estimates between consecutive lens-free raw in-line holograms.

Given multiple sub-pixel shifted raw lens-free holograms (e.g., image frames 30), a higher resolution hologram can be obtained to effectively achieve a smaller pixel size. This super-resolved hologram is synthesized by optimizing the projections of a higher resolution grid (downsampled with the appropriate shifts as calculated using the local gradient-based iterative algorithm discussed above) against the measured lens-free raw holograms. For this optimization procedure, a cost function is calculated which includes the mean square error between each one of these projections and its corresponding raw hologram, with an additional penalty added for high frequency noise to suppress potential reconstruction artifacts.

For each lens-free raw hologram belonging to a given sequence (of N frames), i.e., $H_i$(m,n), i=1, ..., N, the lateral shift and rotation angle ($\hat{\Delta}_x^{(i)}$, $\hat{\Delta}_y^{(i)}$, $\hat{\theta}^{(i)}$) relative to a chosen reference hologram are computed using the estimation procedure described above. In the results presented herein, the calculated rotation angles have been used only to verify that consecutive holographic frames are not significantly rotated with respect to each other. Also, all the integer pixel shifts are subtracted out and the holograms are simply shifted by an integer number of pixels such that the remaining relative shifts are always sub-pixel.

The goal of the pixel super-resolution algorithm is to synthesize a higher resolution hologram which is compatible with all the measured shifted holograms. If the size of each raw hologram is M×N, one starts with an initial guess for the high-resolution hologram $H_{sr}$(k,l) by interpolating a single raw hologram L times in each direction, where one typically chooses L=4. Given a high-resolution hologram, downsampling it by adding up the appropriate groups of L×L high-resolutions pixels should recover the low-resolution measured pixels. Accordingly, a downsampled hologram can be written as:

$$\tilde{H}_i(m,n) = \sum_{i,j=1,\ldots,L} H_{sr}(mL + [\Delta_x^{(i)}] + i, nL + [\Delta_y^{(i)}] + j) \times W_{i,j} \quad (4)$$

where the square brackets $[\Delta_x^{(i)}]$ approximate the sub-pixel shifts to align with the nearest high-resolution grid, and the weights $W_{i,j}$ represent the sensitivity of the physical sensor pixel at different parts of its active area. $W_{i,j}$ is assumed to be of a Gaussian form, though in principle it can simply be measured by accurately focusing light on different regions of an individual pixel and recording the pixel read-out as a function of the focus position.

The super-resolved hologram is found by minimizing the distance (i.e., the cost function, C) between the measured pixel values for all the sub-pixel shifted raw holograms and the pixel values resulting from downsampling of the high-resolution grid. For the cost function the following was chosen:

$$C = \frac{1}{2}\sum_{i,m,n}(H_i(m,n) - \tilde{H}_i(m,n))^2 + \frac{\alpha}{2}\|Y_{hp} * H_{sr}\|^2 \quad (5)$$

The first term on the right hand side of Eq. (5) is the sum of the squared error between the downsampled pixels and measured raw pixels, while the second term is the norm of the high-resolution hologram filtered by a high-pass filter $Y_{hp}$, which has implemented using a Laplacian operator. This last term regularizes the optimization problem and penalizes high-frequency noise. Here $\alpha=1$ was typically used.

The cost function of Eq. (5) is quadratic as a function of the high-resolution hologram pixels, and is minimized by a conjugate gradient method which can be implemented in Matlab using a computer 24. Details regarding this minimization may be found in Luenberger, D., Linear and nonlinear programming, Addison-Wesley: Reading Mass., 1984, which is incorporated by reference herein.

The resulting super-resolved hologram is then input to a twin-image elimination algorithm to recover the high-resolution image of the object. As explained above, the image sensor 22 obtains raw amplitude images. For digital reconstruction of the diffraction patterns there are two approaches that can be used: (1) Back-propagate the Fourier components of the intensity of the diffraction pattern; and (2) Recover the 2D phase of the amplitude of each diffraction pattern. These two techniques independently enabled twin-image free reconstruction. These digital reconstruction approaches can actually be considered to be part of a broader umbrella of Interferometric and Non-interferometric Phase-Retrieval Techniques. In both of these approaches, the transfer function of the Rayleigh-Sommerfeld integral without any approximations has been used for back-propagating the fields.

The first approach mentioned above works with the intensity of the detected diffraction pattern, and is susceptible to the well-known twin image problem. To eliminate the twin image artifact in this first approach a numerical algorithm was implemented that can iteratively clean the reconstructed images from the twin image. In the second reconstruction method, the amplitudes of the lens-free diffraction pattern (rather than their intensities) are used to recover the 2D phase information of the complex diffraction field that was lost during the detection process. Once the entire complex diffraction field is recovered, the microscopic image can be calculated without any twin image artifact through back-propagation of the complex field.

The phase recovery approach treats the detected quantity as the amplitude of a complex diffraction field, and tries to iteratively recover its phase for digital reconstruction. Therefore the phase recovery based reconstruction approach is especially useful for where the cross-interference terms start to dominate over holographic diffraction. As a trade-off, the space-bandwidth product that is required at the detector end is increased by two fold for the phase recovery technique when compared to the first approach, since the latter one does not only deal with the holographic diffraction term, but also deals with self-interference terms.

The reconstruction process can utilize successive fast Fourier transform (FFT) operations, where after the initial FFT of each iteration, transfer function of Rayleigh-Sommerfeld integral without any approximations has been applied to the Fourier components of the diffraction pattern. Because FFT is used, the presented recoveries are also quite fast in terms of digital computation time, with a convergence time within 15 iterations taking less than 0.2 seconds using a Graphics Processing Unit (GPU).

In order to diffract the wavefronts, the angular spectrum approach is used to numerically solve the Rayleigh-Sommerfeld integral. This computation involves multiplying the Fourier transform of the field with the transfer function of propagation through linear, isotropic media, as shown below:

$$H_z(f_x, f_y) = \quad (6)$$
$$\begin{cases} \exp\left(j2\pi z \frac{n}{\lambda}\right)\sqrt{1 - (\lambda f_x/n)^2 - (\lambda f_y/n)^2}, & \sqrt{f_x^2 + f_y^2} < \frac{n}{\lambda} \\ 0, & \text{otherwise} \end{cases}$$

where $f_x$ and $f_y$ are the spatial frequencies and n is the refractive index of the medium.

Two different iterative approaches, as explained above, can be taken in order to reconstruct the image, free from any twin-image artifact. In both methods, the raw diffraction patterns are up-sampled typically by a factor of four to six, using cubic spline interpolation before the iterative reconstruction procedure. Although up-sampling does not immediately increase the information content of the diffraction patterns, it still offers significant improvements for achieving a more accurate phase recovery and higher resolution in the reconstructed image. Through the iterative reconstruction steps detailed below, these higher spatial frequencies gradually attain non-zero energy, which allows sub-pixel resolution in the final reconstruction.

Method 1:

The first method falls under the broad category of Interferometric Phase-Retrieval Techniques and is applicable to cases where the recorded intensity is dominated by the holographic diffraction terms. The first step is the digital reconstruction of the hologram, which is achieved by propagating the hologram intensity by a distance of $z_2$ away from the hologram plane yielding the initial wavefront $U_{rec}$. As a result of this computation, the virtual image of the object is recovered together with its spatially overlapping defocused twin-image. It is important to note that the recorded intensity can also be propagated by a distance of $-z_2$. In this case, the real image of the object can be recovered, while the defocused virtual image leads to the twin-image formation.

In order to eliminate the twin-image artifact, an iterative approach using finite support constraints is utilized. Essentially, this technique relies on the fact that duplicate information for the phase and amplitude exists in two different reconstruction planes at distances $+z_2$ and $-z_2$ from the hologram plane, where the virtual and real images of the object are recovered, respectively. Therefore, a twin-image-free reconstruction in one of the image planes can be obtained, while filtering out the duplicate image in the other plane. Without loss of generality, the real image was filtered out to obtain a twin-image-free reconstruction in the virtual image plane at $-z_2$. The real image of the imaging plane only occupies the region inside its support, while the defocused twin-image image spreads out to a wider region around the object, also overlapping with the real image inside the support. Hence, deleting the information only inside the support ensures that the real image is completely removed from the reconstructed wavefront. Nevertheless, the virtual image information inside the support is also lost, and the iterative technique tries to recover the missing information of the virtual image by going back and forth between the virtual and real image planes, recovering more of the lost information at each iteration.

The steps of twin-image elimination are detailed below.

a) Initially the real image, which is the back-projected hologram at a distance of $+z_2$, is used for determining the object support. Object support can be defined by either thresholding the intensity of the reconstructed image, or searching for its local minima.

b) The region inside the support is deleted and a constant value is assigned to this region as an initial guess for the deleted part of the virtual image inside the support as shown below:

$$U_{z_2}^{(i)}(x, y) = \begin{cases} U_{rec}, & x, y \notin S \\ \overline{U}_{rec}, & x, y \in S \end{cases} \quad (7)$$

Where $U_s^{(i)}(x,y)$ denotes the field at the real image plane after the $i^{th}$ iteration. S represents the area defined by the object support, and $\overline{U}_{rec}$ is the mean value of $U_{rec}$ within the support.

c) Then, the field at the real image plane is back propagated by $-2z_2$ to the virtual image plane. Ideally, the reconstruction at this plane should be free from any twin-image distortions. Therefore, the region outside the support can be set to a d.c. background value to eliminate any remaining out-of-focus real image in the virtual image plane. However, this constraint is applied smoothly as determined by the relaxation parameter $\beta$ below, rather than sharply setting the image to d.c. level outside the support:

$$U_{-z_2}^{(i)}(x, y) = \begin{cases} D - \dfrac{D - U_{-z_2}^{(i)}}{\beta}, & x, y \notin S \\ U_{-z_2}^{(i)}, & x, y \in S \end{cases} \quad (8)$$

where D is the background in the reconstructed field, which can either be obtained from a measured background image in the absence of the object, or can simply be chosen as the mean value of the field outside the object supports at the virtual image plane. $\beta$ is a real valued parameter greater than unity, and is typically chosen around 2-3. Increasing $\beta$ leads to faster convergence, but compromises the immunity of the iterative estimation accuracy to background noise.

d) The field at the virtual image plane is forward propagated to the real-image plane, where the region inside the support now has a better estimate of the missing part of the virtual image. The region outside the support can be replaced by $U_{z_2}^{(1)}(x,y)$ the original reconstructed field at the real image plane, as shown below:

$$U_{z_2}^{(i+1)}(x, y) = \begin{cases} U_{z_2}^{(i)}, & x, y \notin S \\ U_{z_2}^{(i+1)}, & x, y \in S \end{cases} \quad (9)$$

Steps c to d can be repeated iteratively until the final image converges. By replacing the intensity at the detector plane with the measured one, and keeping the updated phase distribution, one can start the next iteration to better estimate the phase of the diffracted field after each cycle. Convergence is achieved after 10-15 iterations, which takes much less than a minute on a computer with a modest hardware configuration.

Method 2:

The second method utilized for eliminating the twin-image is classified under Non-Interferometric Phase-Retrieval Techniques, where the recorded image is treated as the intensity of any diffraction field. Together with the constraint that the imaging field has finite support, this technique is capable of iteratively recovering the phase of the diffracted field incident on the detector from a single intensity image. As a result, the complex field (amplitude and phase), rather than the intensity, can be back-propagated, thereby allowing reconstruction of the objects free from any twin-image contamination. This method can be decomposed into the following steps:

a) The square-root of the recorded diffraction pattern intensity is propagated by a distance of $-z_2$ to the object plane, assuming a field phase of zero as an initial guess. The aim of the algorithm is to iteratively determine the actual phase of the complex field at the image sensor plane, and eventually at the object plane. In the first iteration, the object support is defined either by thresholding the intensity of the field at the object plane, or by locating its regional maxima and/or minima.

b) The field inside the object supports is preserved, while the complex field values outside the supports is replaced by a background value $D_{-z_2}(x,y)$, as shown below:

$$U_{-z_2}^{i+1}(x, y) = \begin{cases} m \cdot D_{-z_2}(x, y), & x, y \notin S \\ U_{-z_2}^{i}(x, y), & x, y \in S \end{cases} \quad (10)$$

where $D_{-z_2}(x,y)$ is obtained by propagating the square root of the background intensity of the image obtained by the same setup in the absence of the cells; and $m = \text{mean}(U_{-z_2}^1(x,y))/\text{mean}(D_{-z_2}(x,y))$.

c) The modified field at the object plane is propagated back to the detector plane, where the field now has a non-zero phase value. The amplitude of this field is replaced with the square root of the original recorded hologram intensity as no modification for the amplitude should be allowed while converging for its phase. Consequently, $U_0^{(i)}(x,y)$, the complex diffraction field at the detector plane after the $i^{th}$ iteration can be written as follows:

$$U_0^{(i)}(x,y) = |U_0^{(0)}(x,y)| \cdot \exp(\emptyset_0^{(i)}(x,y)) \quad (11)$$

where the superscripts denote the iteration step, and $\emptyset_0^{(i)}(x,y)$ denotes the phase of the field after the $i^{th}$ iteration.

Steps a to c can be iterated until the phase recovery converges. Typically, the results presented herein are obtained with less than fifteen (15) iterations, which is quite similar to the first Method.

Experimental Results

To demonstrate the system 10, C. elegans (worm) samples flowing within 0.1 mm tall microfluidic channels that were positioned at ~15° with respect to the sides of a CMOS sensor chip (2.2 μm pixel size) have been imaged. In order to maintain object rigidity during image acquisition, C. elegans samples were temporarily paralyzed using Levamilsole. The samples within the microchannel were then imaged at a depth of ~0.8 mm away from the active region of the CMOS chip using a modest frame rate of 5-6 fps (over 24 mm² field of view), which could be significantly increased (e.g., >20 fps) by digitally selecting a smaller field-of-view of the sensor-chip. For this imaging geometry, the numerical aperture (NA) of each raw lens-free in-line hologram (before pixel super-resolution) is determined by the pixel size and the temporal coherence length of the source; and under similar imaging conditions (with 2.2 μm pixel size) after digital reconstruction of raw lens-free holograms, an NA of about 0.05-0.90 together with a sub-pixel spatial resolution of ~0.5-2.0 μm can be achieved (or less).

The microfluidic device was composed of a rectangular glass channel with inner dimensions of 0.1 mm×2 mm×50 mm (Wale Apparatus). This microchannel was attached to a reservoir on both ends. Copper wires were then inserted into these reservoirs to function as electrodes for driving object movement. For electro-kinetic flow, a voltage of ~2 V was applied between the two ends of the device, creating an object speed of ~1 μm/sec. For pressure driven flow, a pressure gradient was generated by slightly over-filling one of the reservoirs to create an object speed of ~2 μm/sec. This microchannel is placed directly on the top of the protective glass layer of the digital sensor chip, creating an object-sensor vertical distance of approximately 0.8 mm.

A small volume of Nematode Growth Medium containing C. Elegans was suspended in a 1 mM solution of Levamisole, a paralyzing agent. After several seconds of vortexing and centrifugation the worms are extracted by a pipette and injected into the glass reservoirs of the micro-fluidic device.

For imaging, a 5 megapixel CMOS sensor chip was used with 2.2 μm pixel size and a total imaging area of ~24 mm² (Aptina MT9P031STC). The sensor was operated at a frame rate of ~5-6 frames per second to capture the raw lens-free holograms of the flowing objects over a field of view of ~24 mm². For the source, a monochromator with a Xenon Lamp (Cornerstone T260, Newport Corp.) was used. The spectral bandwidth (FWHM) of the illumination as well as the center wavelength was chosen to be around ~5 nm and ~500 nm, respectively. A circular pinhole (aperture 20) of ~50 μm diameter, located ~5 cm above the sensor surface was used to filter the illumination as illustrated in FIG. 1. The power after the aperture was measured to be <10 μW.

Raw lens-free holograms were continuously captured at ~5-6 fps as the objects were flowing through the microchannel due to the applied electric field or the pressure gradient. The microchannel was placed at an angle (~15°) with respect to the sensor edges such that motion along the tube would generate a shift component in both sensor axes directions (x and y). The lateral translation and angular rotation between consecutive frames were simultaneously computed using a local gradient-based iterative algorithm, as described above, which was applied to a 50×50 pixel region located at the center of the holographic pattern of interest.

To evaluate the performance of the system 10, two different flow schemes were tested. First, electro-kinetic flow of the C. elegans samples was employed by applying a DC voltage of ~2 V across two ends of the micro-fluidic channel (cross-section: 0.1×2 mm), which created a speed of ~1 μm/sec for the C. elegans worms. Such a low speed is only needed over a few seconds (e.g., ≤3 sec) of image acquisition after which the samples within the microchannel can be rapidly flushed out using e.g., pressure flow. This object speed can also be significantly increased by applying larger DC voltages together with a higher frame rate over a smaller field of view. Under these conditions, lens-free in-line holograms were continuously captured of the flowing samples, each with an integration time of <50 ms (illumination power: <10 μW). As discussed below, ~15 consecutive frames, corresponding to ~2-3 seconds of image acquisition, are sufficient to synthesize high-resolution images of the samples that are flowing within the microchannel. However, to better illustrate different features of the presented opto-fluidic microscopy technique and to provide image comparisons, frames were continued to be acquired for ~45 seconds, capturing a total of 230 unique lens-free holograms. Typically, the number of image frames may include between about 20 to about 500 frames although, as described herein, even fewer or more frames may be used.

Next, in-plane translation and rotation of these lens-free holograms between consecutive frames was quantified using a local gradient-based iterative algorithm described in Hardie, R. C. et al. which is discussed herein. FIGS. 3A and 3B illustrate, respectively, the two-dimensional (2D) and rotational shifts of the objects driven by electro-kinetic motion. FIG. 3A illustrates the two-dimensional lateral shifts of consecutive holographic frames with respect to the first one. FIG. 3B illustrates in-plane rotation angles of consecutive holographic frames with respect to the first one. As shown in FIGS. 3A and 3B, due to the relatively large cross-section of the microchannel (which permits simultaneous imaging of different objects with a wide range of sizes), there is considerable amount of lateral fluctuation as well as in-plane rotation observed during the flow of the worm.

To recover a high-resolution image of the object, not all of these shifted holograms are required, and in fact starting from an arbitrary initial point in time, only ~15 consecutive frames would be sufficient. To illustrate this, 3 random sub-sequences were chosen. These are identified as Sequence A, B and C as highlighted in FIGS. 3A and 3B, each of which contains 15 consecutive lens-free holograms of the moving sample acquired over ~3 seconds. To test a more challenging imaging condition, Sequence C was chosen within a region where there is considerable rotation of the sample between the consecutive frames as quantified in FIG. 3B. FIG. 3C shows the relative shifts of these holographic frames with respect to the first frame of each sequence (Sequence A: circle data points, Sequence B: square data points and Sequence C: diamond data points). In FIG. 3C, only the sub-pixel shifts are shown, since any integer number of pixel shifts does not contain additional information for synthesis of a super-resolved hologram. These were digitally subtracted out for the data of FIG. 3C.

To digitally synthesize a super-resolved hologram from a given sequence of lens-free raw holograms, a cost function that is defined by the mean square error between the undersampled versions of the high-resolution hologram and each one of the measured frames (described above) was iteratively minimized. This step ensures that the synthesized super-resolved hologram would satisfy (with the least possible error) all the lower-resolution sub-pixel shifted raw holograms of a given sequence captured during the microfluidic flow of the object. To stabilize this optimization process against artifacts, a penalty was added to the cost function for high-frequency noise. This cost function is then iteratively minimized using a conjugate gradient method described in Hardie, R. et al., Joint MAP registration and high-resolution image estimation using a sequence of undersampled images, IEEE Trans. on Image Process. 6, 1621-1633 (1997) implemented in Matlab, which took ~2.5 seconds to converge on a 3.2 GHz PC. The aforementioned Hardie et al. publication is incorporated by reference herein. This computation time can be reduced by at least an order of magnitude using a Graphics Processing Units (GPU), and additional enhancement can be achieved by computing different down-sampled holograms (corresponding to different sub-pixel shifts) all in parallel.

Based on this optimization routine, for each one of the sub-sequences (15 frames) shown in FIGS. 3A and 3B a super-resolved, high resolution hologram of the worm within the micro-fluidic channel has been created. FIG. 4A illustrates a super-resolved, high resolution hologram image using Sequence A. FIG. 4B illustrates an enlarged section of FIG. 4A where sub-pixel holographic oscillation is observed. FIG. 4C illustrates a single lens-free raw hologram (low resolution) image of the same worm to better present the increased fringe visibility of the synthesized hologram.

This super-resolved hologram is then rapidly processed using the iterative twin-image elimination algorithm described herein, to reconstruct a higher resolution image of the worm (both amplitude and phase) as shown in FIGS. 5A-5E. This reconstruction takes around 15 iterations to converge, which is computed in less than 0.2 sec using a GPU. For comparison purposes, FIG. 5A illustrates a single raw lens-free hologram at a lower resolution image of the object after twin image elimination. FIG. 5E illustrates a conventional transmission microscope image of the same sample acquired using a 40× objective lens (NA=0.65). FIG. 5B illustrates the higher resolution amplitude and phase images of the worm using Sequence A. To further illustrate the performance of the system, FIGS. 5C and 5D show, respectively, the reconstruction results (high resolution amplitude image) of the other two selected sub-sequences (Sequence B and C of FIG. 3A), both of which nicely match to the reconstruction results of Sequence A. FIG. 5B clearly demonstrates the finer resolution of the microscopic images obtained from the super-resolved holograms, validating the system. Furthermore, despite uncontrolled rotation and transverse shift of the sample during the flow, the close similarity among the imaging results of Sequences A, B and C highlights the robustness of this approach to varying flow conditions.

To further investigate the imaging behavior of the system, the reconstruction results were analyzed for a varying number of consecutive holographic frames. FIGS. 6A-6E illustrate respectively, high resolution amplitude images using 1, 5, 15, 25, and 100 consecutive frames. The images show progressive enhancement with increasing number of frames, however, additional frames beyond 15 do not appear to offer further enhancement. Approximately three seconds were required to capture 15 frames at 5 fps, and a faster frame rate would allow significant reduction in image acquisition time.

The optimal number of frames and the optimal imaging duration depend on the speed of flow in the channel, the angle of flow as well as the frame rate of the sensor-chip. A faster frame rate along with an appropriately faster flow would further reduce the imaging time of each object within the microchannel.

These experiments validated that regardless of the starting point, ~15 consecutive frames could synthesize a high-resolution image. Furthermore, they also highlight another interesting property of the system, i.e., the acquired sequence of lens-free raw holograms provides not only high-resolution images of the samples within a micro-fluidic channel but also can quantify the flow properties of the same objects, including dynamic speed, lateral shift as well as in-plane rotation, without affecting the image quality.

In a separate experiment, an even more demanding imaging condition was tested, where this time the flow was driven by fluidic pressure differentially applied to the ends of the same micro-fluidic channel, creating an object speed of ~2 μm/sec. Because of the large cross-section of the microchannel such a pressure based fluidic flow is expected to introduce even more rotation as well as lateral drifts during the flow of the samples. Furthermore, since the inner surfaces of the microchannel have not been treated by any special chemistry step, debris adhering to the surface and surface roughness also contribute to the non-uniform nature of the flow. This is indeed what was experimentally observed, as shown in lateral and rotational shifts as seen in FIGS. 7A and 7B. FIGS. 7A and 7B illustrate the object flow characteristics using ~260 holographic frames, however, similar to the previous electro-kinetic case, only ~15 consecutive frames were sufficient for synthesis of super-resolved holograms of the flowing objects. As in the electro-kinetic case, three different random sub-sequences (Sequences A, B and C) were chosen, each composed of 15 frames.

FIG. 7C illustrates sub-pixel shifts of 3 sequences (A, B and C), each composed of 15 consecutive frames are shown. These three sequences of lens-free raw holograms are used independently to generate three different high resolution images as shown in FIGS. 8B, 8C, and 8D. When compared to FIG. 3B, it is evident that the rate of rotation is much higher for pressure driven flow. The consecutive lens-free hologram frames were processed to recover higher resolution images (both amplitude and phase) of the worm as shown in FIGS. 8B, 8C, and 8D, which nicely match to each other as well as to a conventional microscope image of the same sample. FIG. 8A illustrates a single frame, lower resolution image of the worm after twin image elimination. FIG. 8E illustrates a 10× microscope objective lens image (NA=0.25) of the worm for comparison purposes. This *C. elegans* was too large to fit the field of view of the 40× microscope objective lens.

FIGS. 9A-9E illustrate, respectively, reconstruction results of 5, 15, 25 and 100 consecutive holographic frames, which arrive at the same conclusion as in the case of electro-kinetic flow presented in FIGS. 6A-6E. Namely, additional frames beyond 15 do not appear to offer further enhancement. In fact, since the pressure flow induced more rotation of the sample compared to the electro-kinetic flow, the reconstructed image is blurred when using 100 consecutive frames since there is increased rotation among different frames in the sequence. This can potentially be eliminated by making use of the calculated rotation angles to re-align each lens-free holographic frame to each other. This additional step was not needed, however, because 15 frames were sufficient to reconstruct a high-resolution image. Thus, even under pressure-driven flow conditions, which exhibit a significant amount of lateral drift and in-plane rotation of the object, the system performed very well for all the sub-sequences of frames regardless of the time origin of image acquisition.

Figure 10:
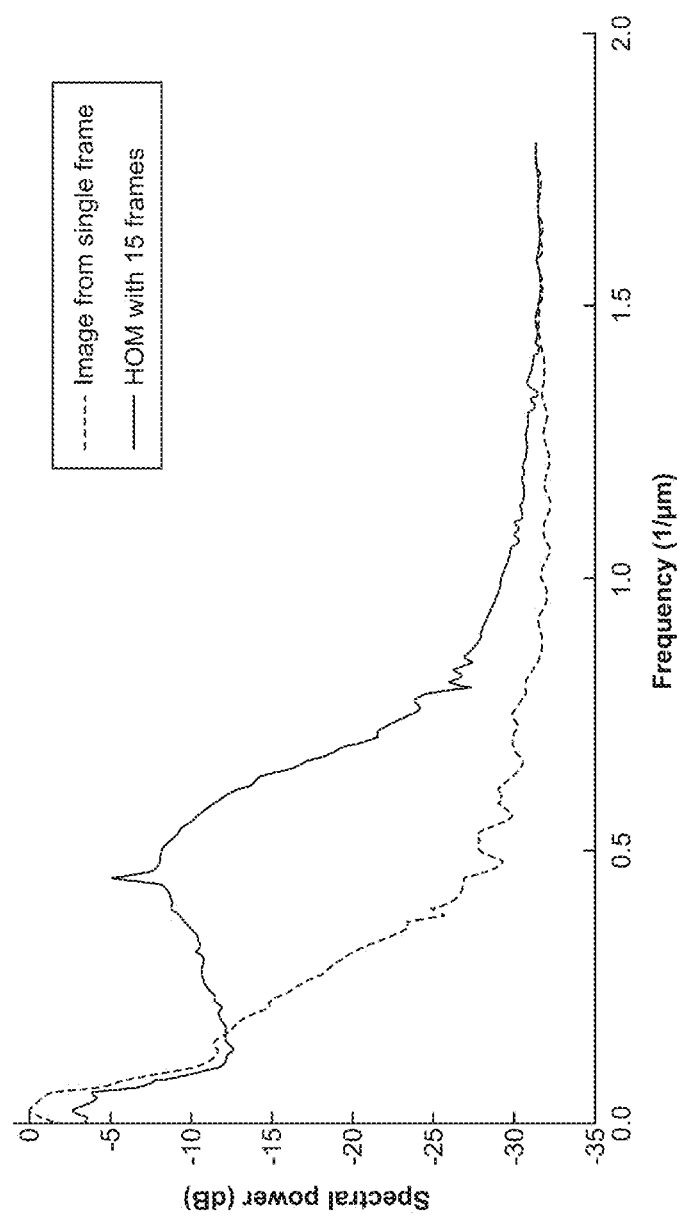
FIG. 10 illustrates the comparison of the radial power spectral density of a high resolution image (15 consecutive frames) and an image reconstructed from a single lensfree raw hologram. The radial frequency bandwidth is approximately doubled using the system and method described herein, leading to a doubling of the effective numerical aperture of the image, when compared to the reconstruction results of a raw lensfree hologram.

As far as spatial resolution is concerned, the system and method described herein is fundamentally limited by the detection signal to noise ratio, as all other digital microscopy modalities are. If the signal to noise ratio of each pixel is further improved, one could potentially create a denser grid for the super-resolved hologram with an effective pixel size that is much less than the physical pixel size (e.g., <400 nm). In the experiments described above, the CMOS chip was kept at room temperature and the main source of noise was the relative intensity noise as well as fixed-pattern noise of the sensor. With the next generation sensor-arrays, further improvements in imaging performance can be expected. In an attempt to quantify the effective numerical aperture of the presented technique, the radial power spectral density of a high resolution image (synthesized from 15 consecutive frames) is compared against the reconstruction results of a single lens-free raw hologram, the results of which are presented in FIG. 10. Because the image spatial bandwidth is approximately doubled by using the holographic method disclosed herein, one can conclude that the effective NA of the results is ~0.3-0.4, roughly twice the NA achieved by reconstruction of a single raw hologram.

While embodiments have been shown and described, various modifications may be made without departing from the scope of the inventive concepts disclosed herein. The invention(s), therefore, should not be limited, except to the following claims, and their equivalents.

What is claimed is:

1. A system for imaging a moving object within a microfluidic environment comprising:
   a flow cell configured to carry the moving object within a flow of carrier fluid;
   an illumination source configured to illuminate a first side of the flow cell through a spatial filter interposed between the illumination source and the flow cell;
   an image sensor disposed on a second, opposite side of the flow cell, the image sensor having an imaging plane that is located at a distance $z_2$ from the flow cell, the imaging plane defined by an array of pixels in orthogonal x and y directions, and wherein the flow cell is located a distance $z_1$ from the spatial filter and $z_2 \ll z_1$, wherein the flow cell is angled relative to an edge of the array of pixels of the image sensor between a non-zero angle and less than 45° so as to generate a shift component on the imaging plane in both the x and y directions;
   at least one processor configured to receive a plurality of image frames of the moving object from the image sensor, each image frame having a low resolution hologram with sub-pixel shifts in the x and y direction as a function of time, wherein the at least one processor generates a super resolved hologram using the sub-pixel shifted lower resolution holograms; and
   wherein the at least one processor eliminates a twin image artifact so that the super resolved hologram yields the recovery of a high resolution image of the object.

2. The system of claim 1, wherein the plurality of image frames comprises 500 or fewer image frames.

3. The system of claim 1, further comprising a display configured to display the reconstructed image.

4. The system of claim 1, wherein the illumination source comprises an at least partially coherent light source having a spatial coherence diameter between about 0.1-10,000 μm.

5. The system of claim 1, wherein the illumination source has a spectral bandwidth within the range of about 0.1 to 100 nm.

6. The system of claim 5, wherein the illumination source is one of a laser, LED, or light bulb.

7. The system of claim 1, wherein the object comprises a cell.

8. The system of claim 1, wherein the at least one processor comprises a computer.

9. The system of claim 1, wherein the flow cell comprises a microfluidic channel.

10. A method of imaging a moving object within a microfluidic environment comprising:
    illuminating a first side of a flow cell configured to carry the moving object within a flow of carrier fluid with an illumination source emitting at least partially coherent light, the at least partially coherent light passing through an aperture prior to illuminating the flow cell;
    acquiring a plurality of lower resolution image frames of the moving object with an image sensor disposed on an opposing side of the flow cell, wherein the image sensor has an imaging plane that is located at a distance $z_2$ from the flow cell, the imaging plane defined by an array of pixels in orthogonal x and y directions, and wherein the flow cell is located a distance $z_1$ from the aperture and $z_2 \ll z_1$, and wherein the flow cell is angled relative to an edge of the array of pixels of the image sensor between a non-zero angle and less than 45°, each image frame having a hologram with sub-pixel shifts in the x and y direction as a function of time so as to generate a shift component on the imaging plane in both the x and y directions;
    generating a super resolved hologram using the sub-pixel shifted holograms and downsampled pixels from a higher resolution grid; and
    eliminating a twin image artifact so that the super resolved hologram yields the recovery of a high resolution image of the object.

11. The method of claim 10, wherein the plurality of image frames comprises 500 or fewer image frames.

12. The method of claim 10, further comprising displaying the higher resolution image on a display.

13. The method of claim 10, wherein the higher resolution image is reconstructed by at least one processor operatively connected to the image sensor.

14. The method of claim 10, wherein the moving object comprises a cell.

15. The method of claim 10, further comprising compensating for lateral and rotational shifting by minimizing a cost function between downsampled pixels of the high resolution grid and measured raw pixels from the low resolution image frames.

16. The method of claim 10, wherein the reconstructed higher resolution image has an effectively increased numerical aperture (NA) that achieves a higher resolution compared to that of an unreconstructed image.

17. The method of claim 10, wherein the reconstructed higher resolution image has an effective pixel size that is smaller than the pixel size of the image sensor.

18. The method of claim 17, wherein the reconstructed higher resolution image has an effective pixel size that is <2.0 μm and the pixel size of the image sensor is ≥2.0 μm.

19. The method of claim 17, wherein the reconstructed higher resolution image has an effective pixel size that is ≤0.5 μm and the pixel size of the image sensor is ≥2.0 μm.

* * * * *